United States Patent [19]

Hougen

[11] Patent Number: 5,658,221

[45] Date of Patent: Aug. 19, 1997

[54] PORTABLE PERSONAL BREATHING APPARATUS AND METHOD OF USING SAME

[76] Inventor: Everett D. Hougen, 5463 Sugarbush, Flint, Mich. 48503

[21] Appl. No.: 478,741

[22] Filed: Jun. 7, 1995

Related U.S. Application Data

[63] Continuation-in-part of Ser. No. 386,375, Feb. 10, 1995.

[51] Int. Cl.$^6$ .................................................. A63B 23/18
[52] U.S. Cl. .................................................. 482/13; 601/41
[58] Field of Search ........................ 482/13; 128/200.24; 601/41, 42, 43, 44; 84/93, 465, 466, DIG. 14

[56] References Cited

U.S. PATENT DOCUMENTS

| | | |
|---|---|---|
| 3,079 | 5/1843 | Rose . |
| D. 321,227 | 10/1991 | Norell . |
| 515,637 | 2/1894 | Wilhide . |
| 635,232 | 10/1899 | Carroll . |
| 737,008 | 8/1903 | Nichol . |
| 940,735 | 11/1909 | Schaeffer et al. . |
| 1,392,700 | 10/1921 | Oyen . |
| 2,292,474 | 8/1942 | Paxton . |
| 3,298,362 | 1/1967 | Lippitt, Jr. et al. . |
| 3,333,844 | 8/1967 | Jurschak . |
| 3,810,461 | 5/1974 | McCormick . |
| 3,826,247 | 7/1974 | Ruskin et al. . |
| 3,863,914 | 2/1975 | O'Connor . |
| 3,908,987 | 9/1975 | Boehringer . |
| 3,949,984 | 4/1976 | Navara . |
| 4,025,070 | 5/1977 | McGill et al. . |
| 4,054,134 | 10/1977 | Kritzer . |
| 4,062,358 | 12/1977 | Kritzer . |
| 4,114,616 | 9/1978 | Brown ........................... 482/13 |
| 4,155,547 | 5/1979 | Savio et al. ................... 452/127 |
| 4,158,360 | 6/1979 | Adams . |
| 4,221,381 | 9/1980 | Ericson . |
| 4,275,722 | 6/1981 | Sorensen . |
| 4,291,704 | 9/1981 | Petty et al. . |
| 4,345,605 | 8/1982 | Gereg . |
| 4,403,616 | 9/1983 | King . |
| 4,444,202 | 4/1984 | Rubin et al. . |
| 4,473,082 | 9/1984 | Gereg . |
| 4,533,137 | 8/1985 | Sonne . |
| 4,601,465 | 7/1986 | Roy . |
| 4,635,647 | 1/1987 | Choksi . |
| 4,739,987 | 4/1988 | Nicholson . |
| 4,770,413 | 9/1988 | Green . |
| 4,854,574 | 8/1989 | Larson et al. . |
| 4,973,047 | 11/1990 | Norell . |
| 4,981,295 | 1/1991 | Belman et al. . |
| 5,018,517 | 5/1991 | Liardet . |
| 5,154,167 | 10/1992 | Hepburn . |
| 5,165,393 | 11/1992 | Kawaguchi . |
| 5,193,529 | 3/1993 | Labaere . |
| 5,263,908 | 11/1993 | Chen ........................... 482/127 |

FOREIGN PATENT DOCUMENTS

| | | |
|---|---|---|
| 2379291 | 9/1978 | France ........................... 482/13 |

*Primary Examiner*—Jeanne M. Clark
*Attorney, Agent, or Firm*—Howard & Howard

[57] ABSTRACT

A breathing apparatus and method of using the apparatus for exercising the lungs of a user. The breathing apparatus has a main body with a generally cylindrical inner cavity. The main body has a main aperture for the user to breathe into and at least two sets of outer openings. An inner cylinder is coaxially disposed within the inner cavity of the main body and is adapted to move relative to the main body. The inner cylinder has an open end adjacent the main aperture, and at least two sets of inner openings selectively matable with the openings in the main body upon movement of the inner cylinder with respect to the main body. By selecting the appropriate alignment of openings, either resistive, percussive, or pulsing breathing exercises can be performed.

18 Claims, 1 Drawing Sheet

U.S. Patent     Aug. 19, 1997     5,658,221
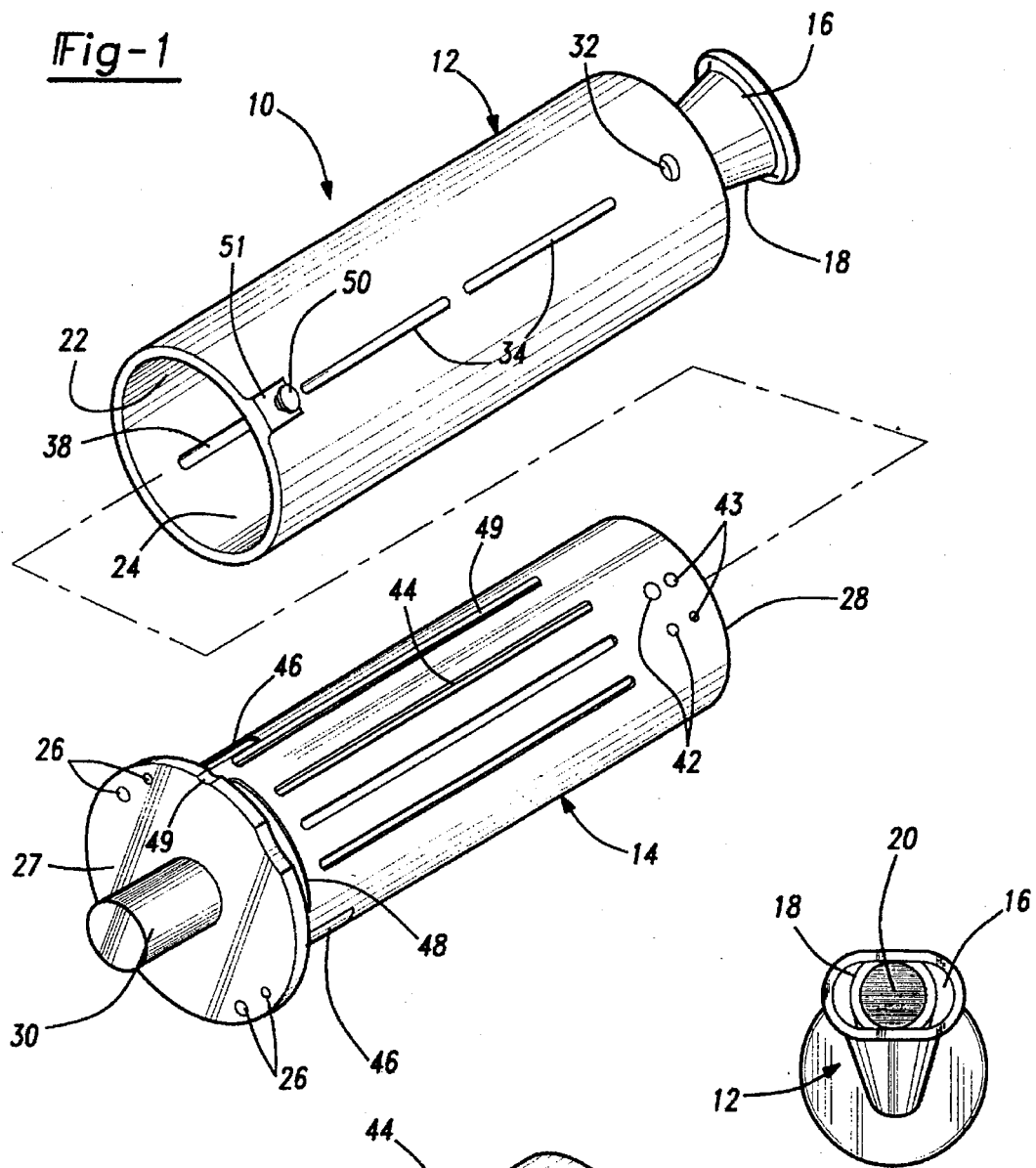
Fig-1
Fig-2
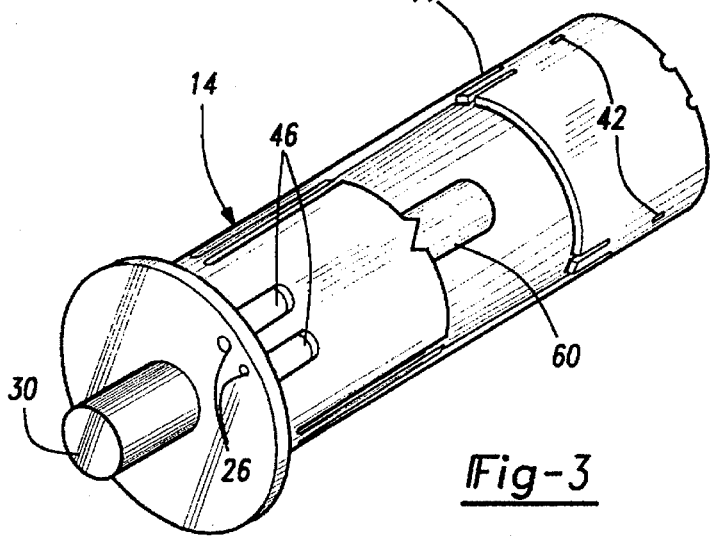
Fig-3

PORTABLE PERSONAL BREATHING APPARATUS AND METHOD OF USING SAME

BACKGROUND OF THE INVENTION

This application is a continuation-in-part of U.S. patent application Ser. No. 08/386,375 filed on Feb. 10, 1995.

The present invention relates to a portable respiratory exercise apparatus providing resistance and intra-trachea bronchial percussion on inspiration and expiration to increase pulmonary efficiency, while improving cilial movement which assists mobilization of intrabronchial mucous or secretions within the lungs.

Research has shown that by practicing deep abdominal breathing, abdominal muscle pressure and temperature are raised, digestion and absorption of foods are improved and pulmonary efficiency is increased. In addition, taking deep breaths while performing little physical movement causes a superfluous amount of oxygen to be made available. Because the large muscular tissue is not consuming the oxygen an increased oxygen supply is made available for many other body systems, such as the brain and the heart.

Forcible and prolonged inspiration and expiration causes a greater expansion and collapse of the air vesicles (alveoli), especially those deep in the lung tissue. By providing resistance to inspiration and expiration, pulmonary muscles are strengthened and developed, thereby allowing a freer and greater exchange of oxygen and carbon dioxide. Persons suffering from lung ailments, healthy persons, and athletes can all improve their pulmonary efficiency through forcible and prolonged inspiration and expiration against resistance.

Some people are able to take only shallow breaths because they are suffering from lung ailments such as asthma, emphysema, chronic bronchitis, chronic obstructive pulmonary disease, or other ailments which reduce the oxygen/$CO_2$ exchange. Frequently, patients recovering from abdominal surgery experience pain during deep breathing and may therefore restrict their own breathing to shallow breaths. In both of the above situations, recovery is slowed because the patients suffer from reduced exchange of oxygen and carbon dioxide in the tissue. Further, the patients are at risk of developing atelectasis because their lungs are not being fully expanded. Atelectasis is a partial collapse of the lungs, possibly leading to necrosis of the lung alveoli. This exacerbates any ailments from which the patient may be suffering by causing poor oxygen exchange in the lungs and possibly resulting in pneumonia.

Patients with emphysema further suffer from mucous blockages in the lungs. Cilia, tiny hairlike structures in the lungs, become flattened down and dogged by mucous. Vibration of the air during inspiration or expiration can cause vibration of the lungs, lung passages (bronchi), and cilia of the patient. This vibration sometimes provides relief to the patient by bringing the cilia to an upright position and mobilizing the mucous, facilitating the expectoration thereof.

Known respiratory exercisers utilize a ball inside a large tube. A user exhales or inhales through a smaller attached tube, causing the ball to rise proportionally to the rate of airflow. However, these known respiratory exercisers only provide resistance to inspiration or expiration, but not both. Further, the large tube must be-maintained in a vertical position in order for the respiratory exerciser to operate correctly. This is inconvenient for persons suffering from lung ailments who may be confined to bed and for athletes who wish to restrict respiratory volume flow during exercise. Still further, this respiratory exerciser does not provide a percussive effect on the user; i.e., a vibration of the air on inspiration or expiration.

Another known respiratory exerciser provides a mask which allows air to be inhaled freely and provides resistance against the expiration of air. The masks do not provide resistance to inspiration and do not provide vibration. Further, the masks are too large to be conveniently portable.

Another respiratory exerciser provides a vibration effect upon expiration. A patient exhales into a tube connected to a conical element loosely supporting a ball. When a patient exhales through the tube, the ball is displaced from the conical element causing an oscillatory movement of the ball, thereby generating a variable pressure opposing the expiration. There are several disadvantages to this device. It does not provide vibration of air during inspiration. It is inconvenient for some patients because it must be maintained at a horizontal position during use. Further, the device provides only varying oscillations in air pressure, rather than a sharp percussion of the air by rapid bursts of air pressure from complete opening and closure of the air passages.

Another respiratory exerciser provides a vibration effect upon either inspiration or expiration by using a pair of adjacent air passageways each containing a reed. Each passageway contains a valve utilizing a coil spring to allow either inspiration or expiration. The compression of each spring can be adjusted to vary the resistance to inspiration and expiration independently. As the patient inhales through one passageway and exhales through the other, air flowing past each reed causes each reed to rapidly vibrate, causing a vibration effect on the lungs of the patient. However, adjustment of the coil spring compression during inspiration and expiration is not convenient. Further, vibration of the air is not as effective as would be a sharp percussion of the air by rapid, complete opening and closure of the air passages.

SUMMARY OF THE INVENTION

The present invention provides a respiratory exercise apparatus which is portable, non-positional, and provides percussion and resistance during inspiration and expiration and pulsing during expiration. The user can select whether to exercise through resistance, percussion, or pulsing. The breathing apparatus has a main body and a movable inner member, which in the preferred embodiment is an inner cylinder. Preferably, both the main body and the inner cylinder have holes and slots for resistance, pulse, and percussion exercises. By rotating the inner cylinder and locking it in place, the desired method of exercise can be selected and performed.

Resistance exercises can be performed by aligning holes in the main body and the inner cylinder. Alignment and locking are accomplished through use of grooves and a locking pin, screw, boss, etc. In the preferred embodiment, the inner cylinder has a plurality of grooves with the grooves being preferably oblong and adapted to receive the locking pin to restrict movement. The oblong grooves allow limited reciprocal movement of the inner cylinder with respect to the main body and prevent rotational movement. This restricted movement allows mating holes to move with respect to one another and automatically vary the resistance as a user inhales and exhales. Alternatively, the inner cylinder can be manually reciprocated to vary the resistance or held in place to maintain a predetermined resistance. In the preferred embodiment, there are several paired holes of varied diameter to give varied resistance. These holes are selected by rotating the inner cylinder, aligning a desired set of holes and locking the inner cylinder in place. In the preferred embodiment, there is a flange that has indicator holes that facilitate easy alignment.

A further resistance exercise can be performed by holding the breathing apparatus generally vertically with the inner cylinder pointing up and exhaling. This will raise the inner cylinder. When the lungs are empty, the inner cylinder automatically drops back into the main body. The user then tries to raise the inner cylinder again by exhaling any remaining air in the lungs. The device is then held with the inner cylinder down, which causes the inner cylinder to automatically drop down. The user then inhales to pull the inner cylinder back into the main body until the lungs are full, which then causes the inner cylinder to drop back down. The exercise is completed by further inhaling to try to raise the inner cylinder.

Percussion exercises can be performed by locking the locking member in a second set of grooves which will align slots in the main body and the inner cylinder. In the preferred embodiment, this groove is formed about the circumference of the inner cylinder to allow limited rotational movement of the inner cylinder with respect to the main body. The user can percuss the lungs by rapidly rotating the inner cylinder while the user inhales and exhales into the main body. Rotation of the inner cylinder moves the slots in the inner cylinder and main body with respect to one another allowing quick bursts of air to enter and exit the users lungs. This provides a strong percussion effect which expands the air vesicles deep in the lungs and loosens mucous blockages in the lungs. Because the present invention provides rapid intermittent complete closure of the airflow in and out of the user's lungs during percussion, a more effective percussion effect is obtained than by merely vibrating the air pressure.

Pulse exercises are performed by aligning the locking device with a longitudinally extending groove. This allows the inner cylinder to reciprocate sufficiently to expose the inner slots. To perform the exercise, the device is held upright, and the user exhales, which causes the inner cylinder to raise, expose the slots, and drop repeatedly. In the preferred embodiment, the inner cylinder is weighted to facilitate the reciprocating action.

In the disclosed embodiments, the respiratory exercise apparatus includes a generally cylindrical main body having at least one main aperture. Although disclosed as cylindrical, in some embodiments, the main body can be non-cylindrical. An inner cylinder is disposed within the main body and can rotate and reciprocate within the main body.

It will be apparent to one of ordinary skill that other embodiments could be used to obtain similar results and objectives and still be within the scope of the invention. With reference to the following Brief Description of the Drawings and disclosure, the invention will be described.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 1 is a perspective view of a respiratory exercise apparatus in accordance with the present invention;

FIG. 2 is an end view of the respiratory exercise apparatus of the present invention as viewed from the mouthpiece.

FIG. 3 is a partially cut away perspective view of a further embodiment of the present invention.

DETAILED DESCRIPTION OF THE INVENTION

With reference to FIG. 1, the breathing apparatus of the present invention is generally shown at 10. The breathing apparatus includes a main body 12 and an inner member 14, which is preferably a cylindrical tube. In the illustrated embodiment, the main body 12 is also illustrated as a cylindrical tube, but it should be understood that the shape of the main body 12 could be any desired shape. Further, if the breathing device does not include the percussion exercise, the inner member 14 could be any desired shape which would allow reciprocal movement with respect to the main body 12. The breathing apparatus is made of Delron, a material supplied by Dupont.

The main body 12 has a mouthpiece 16 attached to a flange 18. The flange 18 is preferably angled at about 45° and includes a bore 20 that communicates with the interior 22 of the main body 12. In the preferred embodiment, the mouthpiece 16 is sufficiently flexible to be stretched over flange 18 to change the angle of the mouthpiece from 45° to generally in line with the main body 12. The opposite end 24 of the main body 12 is open for receipt of the inner cylinder 14. The inner cylinder 14 has a closed end 27 and an open end 28 with the open end 28 being inserted into main body 12. A knob 30 extends from the end 27 so that the inner cylinder 14 can be manually rotated or reciprocated within the main body 12. In the preferred embodiment, the main body is 3.567" long, which includes the mouthpiece 16, and the inner cylinder is 3.67" if the knob 30 is included. The main body and inner cylinder are made of polycarbonate or other moldable plastic, such as polyethylene.

The breathing apparatus 10 is adapted for exercising a users lungs through inspiration and expiration against resistance pulsing and percussion. The apparatus 10 has two sets of openings that can be aligned to provide resistance, pulsing or percussion exercises. By rotating the inner cylinder 14 with respect to the main body 12, the different sets of openings can be aligned and locked in position to allow for a selected exercise.

In the illustrated embodiment, the main body 12 has a hole 32 and a pair of elongated openings or slots 34 and 38 which are about 180° apart. The inner cylinder 14 has a plurality of paired holes 42 and 43 and elongated openings or slots 44 which extend through the inner cylinder 14. These holes 42 and 43 and slots 44 are positioned to align with the holes 32 and elongated slots 34 and 38 respectively as the inner cylinder 14 is rotated with respect to the main body 12. When the holes 42 and 43 are aligned with the hole 32, resistance exercises can be performed. A set of grooves 46 which correspond to the holes 42 are provided in the inner cylinder for holding the inner cylinder 14 with respect to the main body 12. Grooves 46 are adapted to receive a locking member 50 to lock the cylinder in position once an appropriate hole 42 is aligned with hole 32.

When percussive exercises are desired, the slots 34, 38, and 44 are aligned. A different set of grooves 48 are provided, which correspond to the slots 44. Grooves 48 extend circumferentially about the cylinder to restrict movement of the cylinder 14 and main body 12 so that only the slots are aligned for percussive exercises. As will be further described below, the grooves 48 permit limited rotational movement of cylinder 14 with respect to main body 12.

When pulsing is desired, the locking member is inserted into a longitudinally extending groove 49, which extends along the inner cylinder. This groove allows the inner cylinder 14 to reciprocate with respect to the main body 12.

In the disclosed embodiment, the locking member 50 is a small bolt that is threaded into a threaded bore. A raised portion 51 prevents the member 50 from being threaded too far into the grooves. The bolt can be screwed into the groove as desired. It should be understood that other types of locking members could be used, such as a spring loaded detent, a fixed detent, etc.

The grooves 46, which correspond to the holes 32 and 42, are preferably oblong and have their longitudinal axis extending parallel to the longitudinal axis of the inner cylinder 14. Preferably, the locking member 50 has a diameter that is less than the length and width of the groove 46 so that the inner cylinder can reciprocate slightly within the main body 12. Due to the movement of the inner cylinder 14 with respect to the main body 12, the resistance against exhaling can be increased; i.e., the ability to exhale is further restricted, due to the shifting from the hole 43 to the hole 43. When the user inhales, the inner cylinder 14 is pulled back into the main body 12 to shift from hole 43 to hole 42, reducing resistance upon inhalation.

It should be appreciated that by locating the holes 42 and 43 differently, the reverse could be accomplished and greater resistance could be provided when inhaling as opposed to exhaling. Still further, the user can adjust the resistance to inhaling and exhaling by manually sliding the inner cylinder 14 with respect to the main body 12. Again, since the inner holes are sliding with respect to the outer hole 32 in main body 12, the resistance is changed.

In the preferred embodiment, the hole sets 42 and 43 have different diameters to provide varied resistance, depending upon whether the user is exhaling or inhaling. In the preferred embodiment, the diameters of the holes 42 are 0.187", 0.156", 0.125" and 0.093"; the diameters of holes 43 are 0.109", 0.093"; 0.078", and 0.062"; and the diameter of the hole 32 is 0.187". By rotating the cylinder 14, various resistances can be selected and then automatically varied. Further, in the preferred embodiment, there are grooves 46 corresponding to each hole set 42 and 43. Alignment holes 26 are provided in flange 27. These holes 26 correspond in size to their corresponding holes. By locating the holes with the locking member 50, the desired holes 42 and 43 are aligned. Alternatively, by aligning the desired diameter hole 42 with the hole 32, the locking member 50 can be inserted into the adjacent groove. In the disclosed embodiment, there are four (4) sets of holes 42 and 43, four (4) grooves 46 and one hole 32. The holes 42 and 43 are separated into two groups with each set about 180° apart and the hole sets in each group are about 30° apart. The grooves 46 are also separated into two sets with each set about 180° apart and the grooves in each set being about 30° apart. The hole sets 42 and 43 and the grooves 46 are about 90° apart.

With the mouthpiece 16 angled at approximately 45°, the air that escapes from hole 32 blows against the user's face. This provides the user with an indication of the effort being expended and can function as an incentive to continue exhaling effectively.

Percussion is dependent upon grooves 48 which extend between the grooves 46 and correspond to the alignment of the inner slots 44 and the outer slots 34. In the preferred embodiment, each groove 48 extends circumferentially about the inner cylinder through an arc which is greater than 90°. When the locking member 50 is positioned in one of the grooves 48, the inner cylinder 14 can be rotated with respect to the main body 12 through an arc defined by the groove; i.e., approximately 90°. When the inner cylinder 14 is rotated, the slots 44 sweep by the slots 34 to rapidly open and close the slots and rapidly block and open the ingress and egress of air into and out of the breathing apparatus 10. This rapid action causes a percussive result in the users lungs. It should be appreciated by those of ordinary skill in the art that this invention permits percussive exercising of the lungs on inhalation and exhalation.

In the disclosed embodiment, the grooves 48 are positioned apart by about 180°. Each groove is adjacent the end of the slots 44 and extends circumferentially beyond the slots a slight distance to enhance the percussive effect the user receives upon use. Preferably, there are two sets of slots 44 and two grooves 48. Only one set of slots 44 and grooves 48 are shown. Additionally, there are preferably two sets of slots 34 on opposed sides of main body 12. The groove 48 opposite the aligned slot 44 is the groove that receives the locking member 50. It should be appreciated that the groove 48 adjacent the slot 44 could be used if the locking member or the slot 34 were repositioned during manufacture.

In the preferred embodiment, the slots 34 and 44 are long and narrow to give increased percussive effect to the user. The disclosed slots 34 and 44 are approximately two (2) inches long and 0.062 inches wide. For strength, each of the slots 34 and 44 can be formed by two smaller slots positioned end to end. Applicant has found that long narrow slots provide a more effective percussion of the lungs because greater volumes of air can rapidly pass through the slots, and the slots can be closed rapidly, resulting in bursts of air into the lungs. Because of the burst of air, a humming noise is produced, which can also act as an incentive for increased usage. A notch 49 is provided to permit easier alignment of the slots 34 and 44. By aligning notch 49 with locking member 50, the slots are automatically aligned.

To provide pulsing exercise, the groove 46 is aligned with locking member 50. A smaller notch 49 is provided to facilitate proper alignment. By aligning notch 51 with locking member 50, groove 46 is directly beneath locking member 50 and can then receive locking member 50. Groove 46 allows the inner cylinder to reciprocate with respect to the main body 12 as the user exhales. With the unit pointed up, the user exhales and the inner cylinder is raised to expose slots 44. When slots 44 are exposed, the inner cylinder 14 drops down momentarily until pressure from the exhaled air increases in the cylinder 14 to raise it again. This repeated raising and dropping causes a pulsing effect on the lungs.

To use the breathing device, the inner cylinder 14 is rotated with respect to the main body 12 to align either the holes 32 and 42 or the slots 34 and 44 or the groove 46. If resistance exercising is desired, then the holes are aligned. If percussion is desired, then the slots are aligned. If pulsing is desired, then groove 46 is aligned. Once aligned, the locking member 50 is threaded into the adjacent groove. Once the desired exercise is selected, the user inhales and exhales into the mouthpiece 16. If resistive exercising is selected, the inner cylinder 14 reciprocates within the main body 12 to automatically adjust the resistance, or the user can manually control the relative resistance by controlling the amount of reciprocal movement of the inner cylinder 14. If percussion is selected, the inner cylinder 14 is manually rotated by the user as the user inhales and exhales. Knob 30 facilitates rotation of inner cylinder 14 with respect to main body 12. If pulsing is desired, the user uses groove 46.

With reference to FIG. 3, a further embodiment of the present invention is shown. In this embodiment, a weight 60 is positioned in the inner cylinder 14. The weight is illustrated as a rod, but it could be a ball, a disk attached to the flange 27, a spring, etc. The weight 60 facilitates the reciprocal movement of the inner cylinder 14 with respect to the main body 12. The weight 60 forces cylinder 14 out of the main body 12 to further restrict inhalation and exhalation or with pulsing to force cylinder 14 back into the main body 12.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A breathing apparatus comprising:

an elongated main body having a generally cylindrical inner cavity, a main aperture communicating with said inner cavity, and at least a first opening and first elongated slot, spaced longitudinally from said first opening, communicating with said inner cavity;

an inner cylinder coaxially disposed within said inner cavity of said main body and adapted to move relative to said main body, said inner cylinder having an open end communicating with said main aperture, and at least a second opening and first elongated slot, spaced longitudinally from said first opening, with said second opening being selectively matable with said first opening and said second slot being selectively matable with said first slot upon movement of said inner cylinder with respect to said main body;

said inner cylinder being adapted to move relative to said main body to selectively align either said first and second openings or first and second slots, with said other of said first and second openings or slots being closed by said main body;

whereby breathing exercises including resistive exercises when said first and second openings are aligned and percussion exercises when said first and second slots are aligned, can be selectively performed.

2. The breathing apparatus of claim 1, wherein said main body is an elongated hollow tube defining said cylindrical inner cavity with said main aperture at one end and an open opposite end.

3. The breathing apparatus of claim 2, wherein said inner cylinder is an elongated hollow tube having one end closed and the opposite end open, said open end being received within said open end of said main body such that it is adjacent said main aperture.

4. The breathing apparatus of claim 1, wherein said main body and inner cylinder have a longitudinal centerline and said inner cylinder is adapted to reciprocate back and forth along the longitudinal centerline and rotate about the longitudinal centerline with respect to said main body.

5. The breathing apparatus of claim 3, wherein said main aperture is defined by a flange and said apparatus includes a mouthpiece mounted upon said flange;

whereby a user can inhale and exhale through said mouthpiece.

6. The breathing apparatus of claim 5, wherein said inner cylinder includes a plurality of grooves spaced about said inner cylinder and a locking means positioned on said main body for selectively engaging said grooves;

said grooves being associated with said first and second openings and first and second slots to permit selective alignment and restrict subsequent movement.

7. The breathing apparatus of claim 6, wherein said grooves are divided into a first group associated with said first and second openings and a second group associated with said first and second slots.

8. The breathing apparatus of claim 6, wherein said grooves are divided into two sets, with one of said sets having elongated grooves with a longitudinally extending center line that extends generally parallel to a longitudinal center line of said inner cylinder;

said locking device being received within at least one of said elongated grooves, said locking device being adapted to move within said elongated groove;

whereby said inner cylinder can move longitudinally with respect to said main body.

9. The breathing device of claim 8, wherein said interaction of said locking device and said elongated groove closes said slots.

10. The breathing apparatus of claim 1, wherein said inner cylinder and said main body have a plurality of grooves divided into at least first and second groups of grooves and a mating stop member, said first group of grooves having grooves which extend circumferentially with respect to said inner cylinder permitting rotational movement of said inner cylinder with respect to said main body, said stop member mating with said grooves to control the extent of rotational movement, said rotational movement permitting percussive exercising.

11. The breathing apparatus of claim 10, wherein said second group of grooves extend generally longitudinally with respect to said inner cylinder permitting longitudinal movement of said inner cylinder with respect to said main body, said stop member mating with at least one groove of said second set of grooves to control the extent of longitudinal movement, said longitudinal movement permitting resistive exercising.

12. The breathing apparatus of claim 1, wherein said inner cylinder includes a plurality of second openings;

said plurality of second openings each have different diameters;

at least one of said second openings being adapted to mate with said at least one first opening to vary resistance to inhaling and exhaling, said inner cylinder being longitudinally movable with respect to said main body to further vary resistance by sliding said at least one of said second openings with respect to said first opening to partially open and close said first and second openings as a result of inhaling and exhaling.

13. The breathing apparatus of claim 1, further including a stop means adapted to align said first slot and said second slot and to permit limited rotation of said inner cylinder with respect to said main body to allow percussive exercising;

said first and second openings being closed when said grooves are aligned.

14. The breathing apparatus of claim 1, wherein said inner cylinder has a rotation member for permitting manual rotation of said inner cylinder with respect to said main body.

15. The breathing apparatus of claim 1, wherein said breathing apparatus is made of Delron.

16. The breathing apparatus of claim 1, wherein a biasing means is positioned within said inner cylinder to facilitate movement of said inner cylinder.

17. A method for exercising the lungs, said method comprising the steps of:

providing a breathing apparatus having a main body with a longitudinal centerline, said main body having a generally cylindrical inner cavity, a main aperture communicating with said inner cavity, outer slots communicating with said inner cavity and an outer opening communicating with said inner cavity and an inner cylinder coaxially disposed within said inner cavity of said main body said inner cylinder being adapted to reciprocate along the centerline and rotate about the centerline relative to said main body, said inner cylinder having a plurality of inner openings selectively matable with said outer opening, and a plurality of inner slots selectively matable with said outer slots in said main body;

rotating said inner cylinder with respect to said main body to align either said inner and outer slots or said inner and outer openings;

inhaling and exhaling into said main body;

alternatively reciprocating said inner cylinder with respect to said main body to vary the resistance to inhaling and exhaling to provide resistive exercise to the lungs;

rotating said inner cylinder with respect to said main body to intermittently restrict the ingress and egress of air into and out of said breathing apparatus to provide bursts of air into the lungs.

18. The method of claim 17, wherein said breathing apparatus includes a restricting means for restricting movement of said inner cylinder and main body;

said method including the steps of engaging said restricting means after aligning either said slots or apertures.

* * * * *